United States Patent [19]

Lutz et al.

[11] Patent Number: 4,474,678
[45] Date of Patent: Oct. 2, 1984

[54] ALKANOL ETHOXYLATE-CONTAINING DETERGENT COMPOSITIONS

[75] Inventors: Eugene F. Lutz; Donald L. Wood; Hans E. Kubitschek, all of Houston, Tex.

[73] Assignee: Shell Oil Company, Houston, Tex.

[21] Appl. No.: 363,175

[22] Filed: Mar. 29, 1982

[51] Int. Cl.³ .................. C07C 29/06; C07C 43/11; C11D 1/72; C11D 3/075
[52] U.S. Cl. .................. 252/174.21; 252/540; 252/559; 252/DIG. 1; 568/622
[58] Field of Search ............ 568/622; 252/174.21, 252/174.22, 540, 559, DIG. 1

[56] References Cited

U.S. PATENT DOCUMENTS

| | | | |
|---|---|---|---|
| 2,870,220 | 1/1959 | Carter | 252/174.21 |
| 3,350,462 | 10/1967 | Leary | 252/174.21 |
| 3,372,201 | 3/1968 | Leary | 252/174.21 |
| 3,843,563 | 10/1974 | Davies | 252/547 |
| 4,079,078 | 3/1978 | Collins | 252/545 |
| 4,110,262 | 8/1978 | Arnau | 252/545 |
| 4,247,424 | 1/1981 | Kuzel | 252/528 |
| 4,363,756 | 12/1982 | Sepulueda | 252/550 |

OTHER PUBLICATIONS

Union Carbide Bulletin No. F-41449B "Tergitol S Surfactants for the Textile Industry", pp. 28-29, 1970.

Primary Examiner—Dennis L. Albrecht
Attorney, Agent, or Firm—Richard F. Lemuth

[57] ABSTRACT

Detergent compositions particularly useful in hard-surface cleaning comprise an alkanol ethoxylate component which consists essentially of a mixture of compounds of the formula $R-O-(CH_2CH_2O)_x H$, wherein R is an alkyl group of from 8 to 18 carbon atoms, said alkyl group having a linear carbon chain in at least about 50 percent of the ethoxylate molecules; wherein the $-O-(CH_2CH_2-O)_x H$ ether substituent is, in at least 40 percent of the molecules of the mixture, bound to R at a carbon atom which is neither a terminal carbon atom nor a carbon atom adjacent to a terminal carbon atom; and wherein x has an average value for all ethoxylate molecules of the mixture which is in the range from about 3 to 9; said ethoxylate component being further characterized as having a hydrophile-lipophile balance that is between about 10.4 and 12.0; and said composition being further characterized as containing less than about 2 percent by mole, calculated on moles of the mixture of ethoxylate compounds therein, of compounds having a $C_8$ to $C_{18}$ alkyl group substituted by multiple ether substituents.

16 Claims, 1 Drawing Figure

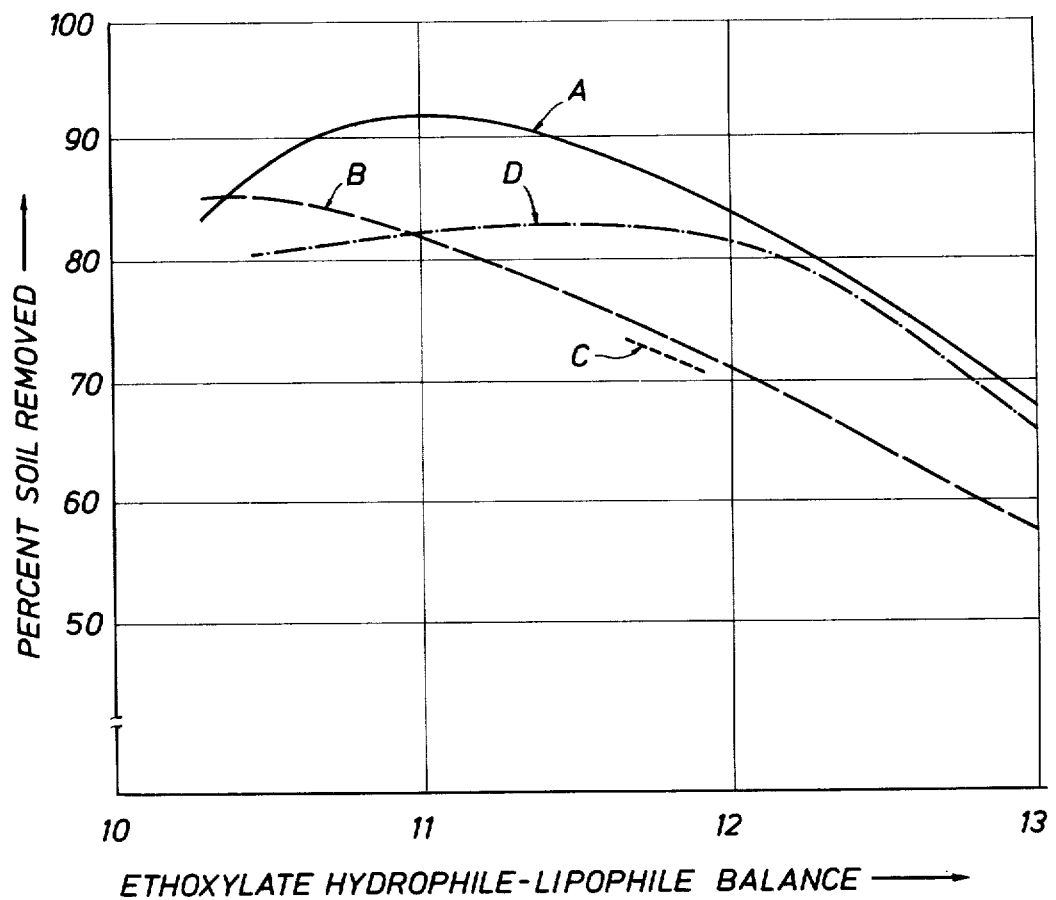

ALKANOL ETHOXYLATE-CONTAINING DETERGENT COMPOSITIONS

BACKGROUND OF THE INVENTION AND DESCRIPTION OF THE PRIOR ART

The present invention relates to detergent compositions comprising alkanol ethoxylate components of particular description.

Certain alkanol ethoxylates, or simply ethoxylates as the terminology is used herein, are known to the art as materials having principal utilities relating to their surfactant properties. Most commonly, such ethoxylates are employed as components of detergent formulations for use in industry and in the home. Because they have very desirable biodegradation characteristics, market demand for the ethoxylates, now estimated to be about six hundred million pounds per year in the United States, is continually growing.

The general class of alkanol ethoxylate compounds of relevance to the invention is characterized by the chemical formula $$R-O-(CH_2-CH_2-O)_xH,$$

wherein R is alkyl and x is an integer greater than or equal to one. Certain ethoxylates within this class are conventionally prepared by the sequential addition of ethylene oxide to the corresponding alkanol (ROH) in the presence of a catalyst.

The most common ethoxylates within this class are the primary alkanol ethoxylates, i.e., compounds of formula I in which the $-O-(CH_2-CH_2-O)_xH$ ether substituent is bound to a primary carbon atom of the alkyl chain R. The present invention, however, more particularly relates to discoveries concerning ethoxylate mixtures comprised in substantial part of secondary alkanol ethoxylates, i.e., compounds of the above formula in which the ether substituent is bound to a secondary carbon atom of the alkyl group.

Secondary alkanol ethoxylates have in the past been commercially prepared by reaction of ethylene oxide with mixtures of secondary alkanols obtained via the oxidation of paraffins. (See, for example, U.S. Pat. No. 3,932,531 and U.S. Pat. No. 2,870,220.) There are suggestions in the art, for instance, U.S. Pat. No. 3,350,462, that secondary alkanols can also be prepared from alpha-olefin mixtures, via sulfation and hydrolysis reactions.

Most particularly, the present invention is directed to novel ethoxylate-containing detergent compositions, wherein the ethoxylate component is characterized by critical definition of the ethoxylate molecules with respect to carbon number of the alkyl chain, number of ethylene oxide adducts in the ether substituent (i.e., the value of x in the above formula), hydrophile-lipophile balance, position of the carbon atom in the alkyl chain to which the ether substituent is bound, and relative content in the composition of compounds having an alkyl group substituted by multiple ether substituents. The prior art is not known to relate critical characterizations in any of these several aspects to the advantageous distinctions now observed between the detergent properties of ethoxylate-containing compositions in accordance with the invention and those of compositions having ethoxylate components of a conventional nature.

SUMMARY OF THE INVENTION

It has now been found that particularly-defined novel alkanol ethoxylate-containing compositions are characterized by certain exceptional surfactant properties, relative to properties of ethoxylate compositions known to the art. In a major aspect of the invention, discovery has been made of certain criticalities associated with the position of ether substitution in the alkyl chain of the ethoxylate molecule. A marked preference is found, with regard to certain desired detergent properties, for compositions having an ethoxylate component that is in substantial part comprised of molecules in which the ether substituent is bound to the alkyl chain at a carbon atom of the chain which is neither a terminal carbon atom nor a carbon atom adjacent to a terminal carbon atom. In other aspects, the invention relates to additional discoveries associated with the properties of such critically-defined ethoxylate compositions. Specifically, it is further found that limitations associated with position of ether substitution in the alkyl chain of the ethoxylate molecules are necessary but not alone sufficient to fully characterize ethoxylate-containing compositions of exceptional detergent properties. For purposes of the invention restriction is, therefore, also placed on the ethoxylate-containing compositions with respect to carbon number of the alkyl chain of the ethoxylate molecules, average number of ethylene oxide adducts in the ethoxylate molecules, hydrophile-lipophile balance for the ethoxylate molecules, and maximum content in the compositions of molecules having an alkyl chain substituted by multiple ether substituents.

Accordingly, in its broader aspects, the present invention is summarily described as directed to an alkanol ethoxylate containing composition wherein the alkanol ethoxylate component is a mixture of alkanol ethoxylate molecules, (1) said mixture characterized as consisting essentially of compounds of the formula $$R-O-(CH_2-CH_2-O)_xH,$$

wherein R is an alkyl group having a carbon number in the range of from 8 to 18 inclusive, with the further provision that in at least about 50 percent of the ethoxylate molecules R is a linear alkyl group; wherein the $-O-(CH_2-CH_2-O)_xH$ ether substituent is bound to R at a carbon atom which is neither a terminal carbon atom nor a carbon atom adjacent to a terminal carbon atom in at least about 40 percent of the ethoxylate molecules; and wherein x has an average value for all molecules of the mixture which is in the range from about 3 to 9, inclusive, with the further provision that x has a value in the range from 3 to 9, inclusive, in at least about 50 percent of the ethoxylate molecules, (2) said mixture being further characterized as having a hydrophile-lipophile balance that is between about 10.4 and 12.0, said hydrophile-lipophile balance being calculated as 880 times the average value of x for the ethoxylate molecules of the mixture, divided by the average molecular weight of the molecules of the mixture, and (3) said composition being further characterized as containing less than about 2 percent by mol, calculated on mols of the alkanol ethoxylate mixture therein, of compounds having a $C_8$ to $C_{18}$ alkyl group substituted by multiple ether substituents.

In certain narrower aspects of the invention, it has also been found that such an ethoxylate component as is described above is prepared as the product of a process comprising steps for the sulfation of substantially linear and internal $C_8$ to $C_{18}$ olefins by reaction with concentrated sulfuric acid, the hydrolysis of the resulting alkyl sulfuric acids to produce secondary alkanols, the reaction of the secondary alkanols with between about 1 and 4 moles of ethylene oxide per mole of secondary alkanol in the presence of an acidic (e.g., Lewis acid) catalyst to prepare a seed ethoxylate mixture, and the reaction of the seed ethoxylate mixture in the presence of an alkaline catalyst with sufficient additional ethylene oxide to produce an alkanol ethoxylate product mixture characterized by an average of between about 3 and 9 ethylene oxide adducts in the ether substituents of the ethoxylate molecules.

BRIEF DESCRIPTION OF THE DRAWING

The drawing illustrates a representative comparison, obtained under standard testing procedures, of the hard-surface cleaning performance of ethoxylate-containing compositions in accordance with the invention (curve A) and a number of compositions having conventional ethoxylate components (curves B, C, and D). The curves show that this cleaning performance, in terms of the percentage of soil removed during the tests, is dependant upon the type of ethoxylate component tested and upon its hydrophile-lipophile balance (HLB). Exceptional detergent performance properties of compositions in accordance with the invention are indicated for ethoxylate components characterized by an HLB value within (and only within) the range from about 10.4 to 12.0.

DESCRIPTION OF THE PREFERRED EMBODIMENTS

For purposes of the description of this invention, an ethoxylate molecule is one generally defined by the formula

R—O—(CH$_2$—CH$_2$—O)$_x$H    (I), wherein R is alkyl and x is an integer greater than or equal to one. The —O—(CH$_2$—CH$_2$—O)$_x$H group is herein termed the ether substituent of the ethoxylate molecule. Compounds having an alkyl group substituted by multiple ether substituents are not referred to as ethoxylates for purposes of the description of the invention.

In essentially all cases of practical interest, preparation and use is made of mixtures of a variety of specific ethoxylate compounds, differing one from the other with respect to the carbon number of the alkyl (R) moiety and/or the structure of the alkyl moiety (e.g., the nature and degree of branching in its carbon structure) and/or the ethylene oxide adduct number (i.e., the value of x in formula I) and/or the position of the carbon atom of the alkyl moiety to which the ether substituent is bound.

The invention relates to the discovery of novel ethoxylate-containing compositions in which the ethoxylate component has critical definition in several of the respects in which an ethoxylate mixture can be characterized, and to exceptional surfactant properties of such compositions in comparison to compositions having an ethoxylate component of conventional nature. In defining an ethoxylate-containing composition of the invention, a restriction upon its ethoxylate component of principal importance relates to the position of the carbon atom in the alkyl group of the ethoxylate molecule to which the ether substituent is bound. For purposes of this invention it is critical that in at least about 40 percent of the ethoxylate molecules the ether substituent is bound to a carbon atom of the alkyl chain which is neither a terminal carbon atom nor a carbon atom adjacent to a terminal carbon atom. (Conversely, in no more than about 60 percent of the ethoxylate molecules is the ether substituent bound to either a terminal carbon atom or a carbon atom adjacent to a terminal carbon atom.) As a general rule, exceptional properties for compositions of the invention are related in a direct manner to the proportion of ethoxylate molecules having this particular position of ether substitution. Accordingly, compositions having an ethoxylate component for which at least about 50 percent of the ethoxylate molecules have ether substitution at a carbon atom that is neither a terminal carbon atom nor a carbon atom adjacent to a terminal carbon atom are preferred, while compositions in which at least about 60 percent of the ethoxylate molecules have such a position of ether substitution are still more preferred and compositions in which at least about 65 percent of the molecules are so substituted are considered most preferred.

While the specified restriction relative to the position of ether substitution in the ethoxylate molecule is necessary for purposes of the invention, this restriction alone is not sufficient to define a composition of exceptional properties in comparison to ethoxylate-containing compositions of the prior art. The desired properties are realized only if further restrictions are also placed on the carbon number and carbon chain structure of the alkyl moiety of the ethoxylate molecules, on the number of ethylene oxide adducts in its molecules, and on the value of the hydrophile-lipophile balance (HLB) for the ethoxylate component.

The ethoxylate component suitably consists essentially of ethoxylate molecules having an alkyl moiety of a carbon number in the range from 8 to 18, inclusive. That is, in greater than about 90 percent (preferably greater than about 95 percent and most preferably greater than about 98 percent) of the molecules of the ethoxylate component, the alkyl moiety is of a carbon number within this range. Greater distinction between the properties of ethoxylate-containing compositions of the invention and those of prior art compositions is observed for molecules with alkyl moieties further specified by narrower carbon number ranges and by greater fractions of molecules with alkyl moieties within the narrower ranges. Thus, for instance, a carbon number range of 10 to 18 (inclusive) is considered preferred, a range of 10 to 16 (inclusive) more preferred and a range of 11 to 15 (inclusive) most preferred. Insofar as the portion of the molecules of the mixture falling within these ranges is concerned, a fraction of at least 50 percent of the ethoxylate molecules within the stated range is preferred, while a fraction of at least 70 percent is more preferred and a fraction of at least 90 percent is considered most preferred. Thus an optimum ethoxylate component for purposes of the invention is one in which greater than about 98 percent of the molecules have an alkyl moiety of a carbon number in the range from 8 to 18 and at least about 90 percent have an alkyl moiety of a carbon number in the narrow range from 11 to 15.

The alkyl moiety of the ethoxylate molecules is necessarily of straight-chain (linear) structure in at least about 50 percent of the ethoxylate molecules. A straight-chain alkyl structure in at least about 70 percent of the ethoxylate molecules is preferred, while such a structure in greater than about 80 percent of the molecules is considered more preferred. Most preferably, about 90 percent or more of the ethoxylate molecules have straight chain alkyl structure.

In terms of the number of ethylene oxide adducts (i.e., the value of the integer x in formula I) the ethoxylate components of compositions of the invention are suitably limited to mixtures of ethoxylate molecules for which the average adduct number (the average value of x) is in the range of from about 3 to 9. Preference may be stated for a range of about 4 to 9. An average ethylene oxide adduct number in the range from about 4.5 to 9 is considered most preferred. Compositions of the invention are further characterized by a relatively narrow distribution of ethylene oxide adduct numbers for the molecules of the ethoxylate mixture. Suitably, at least about 50 percent of the individual molecules have an adduct number in the range from 3 to 9 inclusive. An ethoxylate component in which at least about 60 percent of the molecules have an adduct number in the 3 to 9 range is more preferred, one in which at least about 65 percent of the molecules have an adduct number in this range is still more preferred, and one in which at least about 70 percent of the molecules have an adduct number within this range is considered most preferred.

In addition to independent specifications on both the carbon number of the alkyl moiety and the ethylene oxide adduct number of the ether substituent, it is further necessary for purposes of the invention to place a dependent restriction on these two characteristics of the ethoxylate molecules. This additional restriction is expressed in terms of the hydrophile-lipophile balance (HLB) for the ethoxylate mixture, representing a weight ratio of the relative contributions to the ethoxylate molecules of the hydrophilic ethylene oxide and the lipophilic alkanol molecules from which the ethoxylates are formed. Specifically, HLB for an ethoxylate mixture is herein quantitatively defined as 20 times the average molecular weight of the $-(CH_2-CH_2-O)_x$ ethylene oxide adducts of the ethoxylate molecules of the mixture, divided by the average molecular weight of the ethoxylate molecules of the mixture. Taking into account the molecular weight of 44 for each ethylene oxide adduct, this ratio can also be expressed as 880 times the average value of x (i.e. the average adduct number) for the ethoxylate molecules, divided by the average molecular weight of the ethoxylate molecules.

Distinction in properties has been observed over the prior art only when compositions in accordance with the invention in all other respects are additionally characterized by an HLB value for the ethoxylate component that is in the critical range from about 10.4 to 12.0. An HLB value in the range from about 10.5 to 11.9 is considered preferred, while an HLB value in the range of from about 10.6 to 11.8 is considered more preferred, and an HLB value in the range of from about 10.8 to 11.6 is considered most preferred.

In all cases, each of the specified restrictions and preferences relative to carbon number and linearity of the alkyl moiety of the ethoxylate molecule, to ethylene oxide adduct number of the molecule and to HLB value applies to the complete ethoxylate component mixture as well as to that portion of the complete mixture for which the ethoxylate molecules are characterized by ether substitution at a carbon number of the alkyl moiety that is neither a terminal carbon atom nor a carbon atom adjacent to a terminal carbon atom.

In the prior art, certain conventional ethoxylate-containing compositions contain ethoxylate mixtures which meet the above-described restrictions upon molecular structure. However, these known compositions are not characterized by the advantageous properties discovered for compositions of this invention. For purposes of the invention, it has been found to be necessary to further restrict ethoxylate-containing compositions, otherwise in accordance with the invention to a critically low content of compounds having a single $C_8$ to $C_{18}$ alkyl group with multiple ether substituents. (It should be emphasized that this restriction does not relate to the ethylene oxide adduct number of a single ether substituent, but rather to a plurality of ether substituents bound to a single alkyl group.) Analysis of the secondary alkanol ethoxylate products presently commercially available indicates that they contain a relatively large quantity, for instance, about 5 to 15 percent by mole, calculated on moles of alkanol ethoxylate, of such compounds having a plurality of ether substituents. It is believed that this content in these products of the compounds having multiple ether substitution is characteristic of the manner in which secondary alkanol ethoxylates have been conventionally synthesized, that is, by the ethoxylation of alkanols in the $C_8$ to $C_{18}$ range obtained via paraffin oxidation. Paraffin oxidation products include diols and other polyols with multiple hydroxyl groups, the subsequent ethoxylation of which results in ethylene oxide addition at each hydroxyl position. On the other hand, sulfation and hydrolysis reactions, as can be utilized in the preparation of secondary alkanol ethoxylates in accordance with the invention, convert mono-olefins essentially only to mono-hydric alkanols.

To characterize, for purposes of this invention, a composition of exceptional detergent properties and to distinguish ethoxylate products of the prior art, the composition of the invention is necessarily specified to contain no more than about two percent by mole of compounds having multiple ether substituents bound to a single $C_8$ to $C_{18}$ alkyl group, where this percentage is calculated on moles of the alkanol ethoxylate component in the composition. Preferably, the composition contains less than about one percent by mole of such compounds with multiple ether substituents, while the content of such compounds is more preferably restricted to less than about 0.5 percent by mole and is most preferably restricted to less than about 0.2 percent by mole.

It is considered surprising that compositions of the invention provide meaningful distinction in terms of desirable detergent properties over such related compositions of the art, containing on the order of ten percent by mole of compounds with multiple ether substitution. Like the ethoxylates (herein defined to have single ether substitution) such compounds of multiple ether substitution are known to the art as surfactants. Specific teachings in the art (e.g., U.S. Pat. No. 4,234,444) suggest the inclusion of substantial amounts of such compounds in conventional ethoxylate-containing compositions. It is further considered most surprising that compositions of the invention are distinguishable from these compositions of the art, in terms of particular detergent properties, only for a narrow range of HLB values. Only within an HLB range of about 10.4 to 12.0 (calculated on compounds having either single or multiple ether substitution to the $C_8$ to $C_{18}$ alkyl group) are distinctions observed in the properties of the two types of compositions. Outside of this range the two types of compositions are found to have essentially equivalent detergent performance characteristics.

Optionally, a composition of the invention is also characterized by a limited content of polyethylene glycol compounds, i.e., of the formula $HO-CH_2-CH_2-O)_yH$, where y is an integer greater than one. Such glycol compounds are typically formed as a side product of the reaction of alkanols with ethylene oxide for alkanol ethoxylate preparation, in a quantity of up to about 2 percent by weight, based on ethoxylates. In compositions in accordance with the invention, polyethylene glycol content is preferably less than about 0.5 percent by weight, more preferably less than about 0.3 percent by weight, and most preferably less than about 0.2 percent by weight, calculated on the weight of the alkanol ethoxylate component of the composition.

In light of the above, a variety of processing options will be apparent to those skilled in the art for use in the preparation of ethoxylate components suitable for compositions of the invention. In many general respects, this preparation can be accomplished in a manner similar to processes utilized in the prior art for the manufacture of ethoxylates of conventional character. However, preparation of an ethoxylate mixture meeting the specified critical restrictions on molecular structure will require that particular attention be given to certain processing steps and conditions.

The present invention is considered to encompass, in addition to the ethoxylate-containing compositions described herein, a preferred process for preparation of certain such compositions. A necessary starting material in this process is a mixture of mono-olefins. The restrictions and preferences on carbon number distribution in the mono-olefin mixture are the same as are specified above for the carbon number distribution of the alkyl group of an ethoxylate component suitable for the composition of the invention. Thus, greater than about 90 percent (preferably greater than about 95 percent and most preferably greater than about 98 percent) of the mono-olefins have a carbon number in the 8 to 18 range, while further preference is given to still narrower carbon ranges (i.e., 10 to 18, 10 to 16, and 11 to 15) and to increasing percentages of mono-olefins within each of these narrower carbon number ranges (i.e., 50 percent, 70 percent, and 90 percent). While the olefin starting material may contain materials other than mono-olefins, for instance, the small quantities of paraffins and aromatics which may be found in $C_8$ to $C_{18}$ olefin mixtures prepared by conventional methods, it is necessary to this that the starting material comprise less than about 2 percent (preferably less than about one percent, more preferably less than about 0.5 percent, and most preferably less than 0.2 percent), by mol of olefins having multiple double bonds in the molecule, calculated on the moles of mono-olefin. It is further critical to this process that the major fraction, i.e., at least 50 percent, of the $C_8$ to $C_{18}$ mono-olefins are characterized by an internal position of the double bond. A 70 percent or greater fraction of mono-olefin molecules with internal double bond is preferred, while an 85 percent or greater fraction is considered more preferred and a fraction of 95 percent or more is most preferred. Still further, of the internal $C_8$ to $C_{18}$ mono-olefins, it is desirable that at least about 50 percent be of a linear or straight-chain structure, while linearity in at least about 70 percent of the molecules is preferred, linearity in at least about 80 percent of the molecules is more preferred, and linearity in at least about 90 percent of the molecules is considered most preferred.

In a first process reaction step, the critically-defined olefin starting material is converted into monoalkylsulfuric acids by reaction with sulfuric acid. This sulfation step is suitably conducted under procedures known for reactions of concentrated sulfuric acid with long-chain olefins, for instance, under the methods described in U.S. Pat. No. 2,640,070 to Dahmen and U.S. Pat. No. 4,226,797 to Bakker et al, the teachings of which on olefin sulfation are incorporated herein by reference. Most preferably, sulfuric acid of about 80 to 98 percent concentration is mixed with olefin and with an effective quantity of a reaction modifying agent at a temperature in the range from about 3° to 15° C. (A very suitable modifying agent is the secondary alkanol product of the hydrolysis reaction described hereinbelow.) The monosulfuric acids obtained via sulfation of the mono-olefins are comprised of molecules of the formula $R-OSO_3H$, where R represents an alkyl group of essentially the same definition, with respect to carbon number and carbon chain linearity, as the mono-olefin. When the mono-olefin molecules are in major part of internal double bond position, the sulfation produces a mixture of alkylsulfuric acids in which at least about 40 percent of the molecules have sulfuric acid ester linkage to the alkyl group at a carbon atom which is neither a terminal carbon atom nor a carbon atom adjacent to a terminal carbon atom. The greater the proportion of mono-olefins with internal double bond position (e.g., 70, 85, or 95 percent), the higher is the fraction (e.g., more than about 50, 60, or 65 percent, respectively) of the alkylsulfuric acid molecules with ether linkage other than to a terminal carbon or a carbon atom adjacent to a terminal carbon atom.

The alkylsulfuric acid product of the sulfation reaction is in a second process reaction step subjected to hydrolysis to prepare corresponding alkanols, of the formula $R-OH$, where R is again the alkyl group defined above. If desired, the sulfation product mixture can be first treated, for instance by phase separation, to remove any excess inorganic sulfuric acid reactant. Unreacted olefin (and alkanol reaction modifying agent) can also be removed from the sulfation product if desired but may suitably remain in mixture with the organic acid for purposes of the hydrolysis step. For purposes of the hydrolysis reaction, the alkylsulfuric acids are mixed with water at a temperature in the range of about 5° to 150° C., preferably about 45° to 120° C., and most preferably about 60° to 110° C. In order to maximize conversion to the alkanols the reaction is preferably accomplished during mixing of countercurrent flows of the two substantially immiscible reactants, most preferably in a plurality of contact stages. Alkanols can be separated from the water and inorganic sulfuric acid of the hydrolysis product mixture by phase separation. Olefins (both those not converted to alkylsulfuric acids during sulfation and those formed by reversion in the hydrolysis mixture) are present in the alkanol phase of such a phase separation, and can be removed therefrom by distillation, preferably under vacuum.

The alkanols obtained through the sulfation and hydrolysis reactions are in very great part secondary alkanols. Conversion of the mono-olefins having a terminal double bond yields in great part alkanols in which the hydroxyl group is bound to the alkyl chain at a carbon atom adjacent to a terminal carbon atom. Of the mono-olefins with internal double bonds which are converted to alkanols, a large fraction (typically about 60 to 80 percent) is converted to alkanols having hydroxyl substitution at a carbon atom of the alkyl chain which is neither a terminal carbon nor a carbon atom adjacent to a terminal carbon. Overall, when at least 50 percent of the starting mono-olefins have internal position of the double bond, at least about 40 percent of the alkanol molecules have the hydroxyl group bound to the alkyl chain a carbon atom that is neither a terminal carbon atom nor a carbon atom adjacent to a terminal carbon atom.

In a third reaction step of this process, the alkanol mixture is reacted with ethylene oxide to prepare what is termed a "seed" ethoxylate, having an average number of ethylene oxide adducts per ethoxylate molecule in the range from about 1.0 to 4.0. It is known that, unlike corresponding primary alkanols, the $C_8$ to $C_{18}$ secondary alkanols do not readily react with ethylene oxide in the presence of conventional alkaline catalysts. For this reason, the seed ethoxylation reaction is conducted using a Lewis acid catalyst. It is further known that with such acid-catalyzed ethoxylation, the preparation of an ethoxylate having an average adduct number greater than about 3 is not efficiently accomplished. Thus, to obtain for purposes of this invention an ethoxylate mixture with a higher average ethylene oxide adduct number, the seed ethoxylation is followed by an alkaline-catalyzed reaction of the seed ethoxylate with additional ethylene oxide.

Two-step (acid- and alkaline-catalyzed) ethoxylation of secondary alkanols in this manner is conducted for purposes of this process generally according to procedures known to the art. Thus, the seed ethoxylation is suitably performed by adding ethylene oxide to a mixture of the secondary alkanols and the acid catalyst. Most commonly the liquid alkanol reactant is contacted with ethylene oxide in a reactor with an inert gas cap, e.g., nitrogen. Temperature for this reaction is preferably in the range of about 20° to 160° C., more preferably 40° to 120° C. and most preferably 60° to to 100° C. The reaction is preferably carried out at atmospheric or higher pressure. There is a risk of explosion in ethylene oxide systems maintained in concentrated form at high temperatures and pressures. For this reason, it is preferred that reaction pressure be limited to about 100 psig and that the ethylene oxide concentration in the vapor phase in the reactor not exceed about 50 percent by mole. The reaction can, however, be safely accomplished at higher ethylene oxide concentration and/or higher pressure if suitable precautions (known to the art) are taken. A reaction pressure in the range of about 20 to 100 psig is preferred, while a pressure in the range of about 40 to 80 psig is considered most preferred. For purposes of the invention, the seed ethoxylation is continued until the seed ethoxylate is characterized by an average ethylene oxide adduct number in the range from about 1.0 to 4.0, preferably from about 1.2 to 3.0, more preferably 1.5 to 2.5, and most preferably from about 1.7 to 2.2.

As catalyst for the initial, or seed, ethoxylation reaction of this aspect of the invention, there may be employed any of a number of acidic catalysts as are known in the art for use in ethoxylation reactions. Suitable acidic ethoxylation catalysts include, in a broad sense, the substances classified in the art as Lewis acids or Friedel-Crafts catalysts. Specific examples of these catalysts are the halides (e.g., fluorides, chlorides, and bromides) of boron, antimony, tungsten, aluminum, iron, nickel, tin, zinc, titanium, and molybdenum. Complexes of such halides with, for example, alcohols, ethers, carboxylic acids, and amines have also been reported as effective acidic ethoxylation catalysts. Still other representative examples are sulfuric and phosphoric acids and the perchlorates of magnesium, calcium, manganese, nickel, and zinc. Mention may also be made of metal oxalates, sulfates, phosphates, carboxylates and acetates, of the alkali metal fluoroborates, of zinc titanate, and of the zinc salt of benzene sulfonic acid, although such materials generally yield low conversion or selectivity in the desired reaction. Typically, but not necessarily, the amount of acid catalyst is on the order of 0.01 to 5.0 percent by weight, based on alkanol reactant. Most of the catalysts are suitably active in the amount of 0.03 to 0.25 percent by weight, on alkanol. Preferred acid catalysts are generally those selected from the class consisting of the fluorides, chlorides and perchlorates of zinc, boron, tin, antimony, iron, titanium, and molybdenum, and mixtures thereof. Considered to be most preferred is an acid catalyst selected from the class consisting of zinc perchlorate, zinc chloride, stannic chloride, antimony pentachloride, ferric chloride and boron trifluoride.

Following the acid-catalyzed ethoxylation reaction, the reaction mixture is neutralized, an alkaline catalyst added, and ethoxylation continued to yield the desired higher ethylene oxide adduct mixture. Preferably acid catalyst residues are removed from the seed ethoxylation reaction product mixture before the second ethoxylation step. This is suitably accomplished by washing the mixture with water, preferably with a dilute aqueous solution of an inorganic base, most preferably with a 0.1 to 1.0 percent by weight aqueous solution of an alkali metal hydroxide. Removal of acid catalyst residues before alkaline catalyzed ethoxylation is effective to yield the preferred low content of polyethylene glycol in the final ethoxylate product and also to reduce contamination of the product with other undesirable by-product. Unreacted alkanol is also preferably removed from the seed ethoxylation mixture, for instance, by distillation, before the alkaline catalyzed ethoxylation step.

In the fourth reaction step, seed ethoxylate is reacted with ethylene oxide in the presence of an alkaline catalyst. Conventional alkaline ethoxylation catalysts, for example, the alkali and alkaline earth metals and their oxides, hydroxides, and alkoxides, are suitable for use in this reaction step of the invention. Potassium hydroxide and sodium hydroxide are most preferred alkaline catalysts. The reaction is suitably conducted at a temperature in the range of about 100° to 200° C., preferably 140° to 180° C., and most preferably 150° to 170° C. Reaction pressure is again largely determined by considerations of safety in the handling of concentrated ethylene oxide vapor. A pressure in the range of atmospheric to about 100 psig is preferred, although higher pressure can be employed if proper precautions are taken, for instance if the ethylene oxide is diluted with an inert. A pressure of about 20 to 100 psig is considered more preferred, while a pressure of about 60 to 100 psig is considered most preferred. The alkaline catalyzed ethoxylation reaction is necessarily controlled (via control over the quantity of ethylene oxide reactant) to yield a product ethoxylate mixture characterized by an average ethylene oxide adduct number and by an HLB value in the critical or preferred ranges as noted hereinbefore.

Overall, the processing aspects of the invention can be alternatively expressed as providing improvement in known processes for preparation of ethoxylate compositions, comprising olefin sulfation, hydrolysis, acid catalyzed ethoxylation, and alkaline catalyzed ethoxylation reactions. This improvement centers on the sulfation of olefins having critical definition with respect to its carbon number distribution, double bond position, carbon chain structure, and proportion of mono-olefins relative to olefins with multiple double bonds, and on the production in the alkaline catalyzed ethoxylation of an ethoxylate mixture of critical average ethylene oxide content and HLB value.

A composition of the invention may consist essentially of the specified ethoxylate component, such as, for instance, is prepared by means of the above-described sulfation, hydrolysis, and two-step ethoxylation process. A composition consisting essentially of the ethoxylate is typically a clear liquid of good handling characteristics at room temperature.

Alternatively, a composition of the invention may suitably be a detergent formulation of the general sort as is conventionally made of known ethoxylates. Commonly, but not necessarily, such a formulation would contain the critically-defined ethoxylate component in a quantity between about one and fifty percent by weight. The remainder of such a formulation would be comprised of one or more other components as are conveniently utilized in ethoxylate-containing formulations, for example, other nonionic as well as anionic and cationic detergent active materials, builders, foam promoters, coloring agents, perfumes and diluents.

In detergent applications, dilution is generally made of an ethoxylate-containing composition with water to form a working solution having a relatively low ethoxylate component concentration, e.g., less than one percent by weight. The composition of the invention is also intended to encompass such solutions. However, it has been found that in very dilute solutions, the desired influence of the specified ethoxylate component upon detergent properties is not distinguishable from the influence of ethoxylate components of conventional character. Only for compositions having a concentration of the specified ethoxylate component in excess of about 0.06 percent by weight are the exceptional detergent properties associated with the invention observed. For reasons of a greater degree of improvement over the properties of prior art compositions, a preferred composition in accordance with the invention has a concentration of the ethoxylate component that is about 0.09 percent by weight or more, while a composition having an ethoxylate component in a concentration of at least about 0.12 percent by weight is considered more preferred.

In general, the ethoxylate-containing compositions of the invention have utility in the great variety of detergent applications for which conventional ethoxylate compositions are known to be of value, including laundry, dishwashing, and hard-surface cleaning services. Particular advantage of the unique properties of a composition of the invention is realized in application to hard-service cleaning, for which the composition is preferably, but by no means necessarily, applied in combination with one or more detergent builders, such as, for instance, tetrapotassium pyrophosphate, sodium tripolyphosphate, trisodium phosphate, sodium-metasilicate, sodium carbonate, tetrasodium ethylene diamine tetraacetate, trisodium nitrilotriacetate, potassium hydroxide, sodium hydroxide, potassium silicates, sodium silicates and sodium gluconate.

EXAMPLE 1

The following procedures were followed to prepare an ethoxylate component in accordance with preferred aspects of the invention, wherein the ethoxylate molecules are characterized by alkyl (R) groups that are about 54% m of a carbon number of eleven and about 46% m of a carbon number of twelve; by a linear alkyl group in greater than about 95% of the ethoxylate molecules; by an ether substituent bound to the alkyl group at a carbon atom which is neither a terminal carbon atom nor a carbon atom adjacent to a terminal carbon atom in about 63% of the ethoxylate molecules; by an average number of ethylene oxide adducts for all molecules of the mixture that is about 4.8; by a number of ethylene oxide adducts in the range from about 3 to 9 in at least about 60 percent of the ethoxylate molecules; by an HLB value of 10.8; and by a negligible content (0.1% m or less) of compounds having a $C_8$ to $C_{18}$ alkyl group substituted by multiple ether substituents.

Secondary alkanol was first produced from a $C_{11}$ and $C_{12}$ olefin starting material via sulfation and hydrolysis reactions. Several batches of the alkanol were prepared and then mixed to obtain a larger quantity for ethoxylate preparation. In preparing a representative batch of the alkanol, a stirred mixture of 317 g of 87% sulfuric acid, 60.5 g $C_{11}/C_{12}$ olefin and 33.6 g of secondary alkanol (a product of previous sulfation and hydrolysis of the same $C_{11}/C_{12}$ internal olefin) was reacted for about 15 minutes at a temperature maintained by cooling in the range of about 15° C. to 20° C. The olefin starting material had a carbon number distribution of about 0.2% m $C_{10}$, 54.3% m $C_{11}$, 45.2% m $C_{12}$, and 0.3% m $C_{13}$, and contained about 99% m internal olefin and greater than 95% olefin molecules with linear (straight-chain) carbon structure. After phase separation of the resulting mixture, there was obtained 146.60 g of a crude alkyl sulfuric acid sulfation product. For purposes of the hydrolysis reaction, 144.5 g of the crude alkyl sulfuric acid was mixed with 282.45 g chilled water as temperature was maintained at about 10° C. The hydrolysis mixture was then refluxed for about one hour at about 100° C., cooled to ambient temperature, and separated to recover 92 g of an alkanol/olefin phase. This organic alkanol/olefin phase was neutralized by mixing with 195 g of aqueous 7% $Na_2CO_3$ solution, phase separating to recover the organic phase, mixing the organic phase with a second 195 g of aqueous 7% $Na_2CO_3$ solution, and phase separating to obtain 92.6 g of a neutralized crude alkanol product mixture.

Several crude alkanol product mixtures obtained under such general procedures were blended. Multiple batch distillations under vacuum (0.2 mmHg) were carried out to recover a finished alkanol product containing (as analyzed by gas-liquid chromatography) 52.71% w secondary $C_{11}$ alkanols, 47.26% w secondary $C_{12}$ alkanols, 0.03% w $C_{11}$ and $C_{12}$ olefins, and a small amount of water. Essentially all of the water was subsequently removed by heating the alkanol to 130° C. while sparging with dry nitrogen.

Ethoxylation of the distilled, dried alkanol was performed in two stages. For the first stage, 438 g of alkanol were introduced into a one-liter autoclave reactor and heated to 80° C. under 8 psig nitrogen pressure. A solution of about 0.7 g of stannic chloride catalyst in an additional 19.3 g of alkanol was added to the autoclave. Nitrogen pressure was increased to 20 psig and ethylene oxide added to the reactor at an initial rate of about 1.3 g per minute. Temperature was maintained at 80° C. as a total of 120.2 g of ethylene oxide was added over 1.5 hours, with pressure gradully increasing but not exceeding 54 psig. When ethylene oxide addition was complete, the temperature was raised to 90° C. for 30 minutes. A liquid crude seed ethoxylate product was then withdrawn.

Before the second stage of ethoxylation, the crude seed ethoxylate (about 560 g) was mixed with about 168 g of an aqueous sodium hydroxide solution (0.3% w, pH=12.7) and the mixture stirred for 15 minutes at 90° C. After phase separation, the seed ethoxylate-containing phase was mixed with another 168 g of aqueous sodium hydroxide solution, again at 90° C. for 15 minutes. Phase separation yielded an organic phase of 582 g (a small amount of which was dissolved and suspended water) which was then subjected to distillation under vacuum. During distillation, 216 g of a mixture (comprising water, unreacted secondary alkanol and some lower ethoxylate) was removed overhead, leaving 366 g of seed ethoxylate having an average ethylene oxide adduct number of 1.8, an average molecular weight of 258, and a low (less than 0.1% w) content of polyethylene glycols.

For further ethoxylation of the seed ethoxylate, about 0.12 g of dry sodium hydroxide was added to 65.0 g of the seed ethoxylate, previously nitrogen sparged for 20 minutes and the mixture heated to 135° C. and maintained at that temperature for about one hour with continued nitrogen sparging. The solution was added to the autoclave was then pressurized to about 10 psig with nitrogen and heated to 155° C. Ethylene oxide was introduced at a rate of about 0.5 to 0.6 g per minute for about 65 minutes. A total of 35 g of ethylene oxide were taken up in the course of this ethoxylation step. The reaction mixture was maintained at about 155° C. for 30 minutes after the end of the ethylene oxide addition, then cooled to 29° C., drained from the autoclave and neutralized with about 0.35 g of glacial acetic acid, to yield about 98 g of the desired ethoxylate component, having an average ethylene oxide adduct number of about 5.0.

EXAMPLE 2

Utilizing the general procedures of Example 1, preparation was made of another ethoxylate mixture suitable as the ethoxylate component of a composition in accordance with the invention. In this case, however, the olefin starting material contained about 54.1% m olefins of carbon number 13 and about 45.4% m olefins of carbon number 14 with the balance evenly split between $C_{12}$ and $C_{15}$ olefins, and the second stage ethoxylation, that is, the reaction of the seed ethoxylate with further ethylene oxide in the presence of the sodium hydroxide catalyst, was continued until about 53 g of ethylene oxide had been taken up, yielding about 116 g of ethoxylate mixture having an average ethylene oxide adduct number of about 7.1, and an HLB of about 12.0. The ethoxylate molecules in the linear alkyl group in greater than about 95% of the ethoxylate molecules; by ether substitution to the alkyl group at a carbon atom that is neither a terminal carbon atom nor a carbon atom adjacent to a terminal carbon atom in about 63 percent of the ethoxylate molecules; and by a negligible content of compounds having a $C_8$ to $C_{18}$ alkyl group substituted by multiple ether substituents.

COMPARATIVE EXAMPLE

The general procedures of Example 1 were again followed. In this case, however, the use of a starting material having a high (95%+) content of alpha-olefins resulted in an ethoxylate mixture product not suitable for purposes of the invention.

The alpha-olefins, very predominently of carbon number 14, were used to prepare an ethoxylate product mixture which had an average ethylene oxide adduct number of about 7.2 and an HLB value of about 11.9, but which failed to meet the requirement that in at least 40 percent of the ethoxylate molecules the ether substituent be bound to the alkyl group at a carbon atom which is neither a terminal carbon atom nor a carbon atom adjacent to a terminal carbon atom. Specifically, the use of the alpha-olefin starting material resulted in a product in which only about 26 percent of the ethoxylate molecules were characterized by the specified position of ether substitution, while in about 74 percent of the ethoxylate molecules, the ether substituent was bound to the alkyl group at a carbon atom in the 2 position of the carbon chain.

EXAMPLE 3

To illustrate the criticalities relating to preparation of secondary alkanol ethoxylates from internal olefins, the $C_{14}$ alpha-olefin starting material utilized in the comparative example was subjected to isomerization (using a conventional heterogeneous isomerization catalyst) to produce random interal olefins (without changing olefin chain length or linearity) which were then processed into ethoxylates following the general procedures of Example 1. The resulting ethoxylate product mixture, which was characterized by ether substitution to the alkyl group at a carbon atom which is neither a terminal carbon atom nor a carbon adjacent to a terminal carbon atom in 80 percent of the ethoxylate molecules, by an average ethylene oxide adduct number of about 7.1, and by an HLB value of about 11.9, proved very suitable for purposes of the invention.

TESTS OF DETERGENT PROPERTIES

A standard hard-surface cleaning test method was employed for quantitative evaluation of certain detergent properties of the critically-defined ethoxylate compositions of the invention in comparison to the properties of related ethoxylate compositions not in accordance with the invention. Procedures of this test method are summarized below. The method is similar to that described in *J. Amer. Oil Chemists Soc.*, 46, 520 (1969).

The test method centers on the mechanical scrubbing of an artifically-soiled surface. Cleaning efficiency (soil removal) is determined photometrically. For purposes of the instant comparative tests, the surface was a white standard gauge (0.080 inch) linoleum (Plain "CL"—Saturated Felt Back, manufactured by Krommenie Products, Scotland), meeting Federal Specifications LLF-1238A-Type 1-Class 2 and DDD-C-95, and passing ASTM D-2859 tests. Panels of 4 inches by 17.5 inches were cut from roll stock. Each panel was prepared, before use in the test, by washing with a commercial hand dishwashing liquid, rinsing, and hanging to dry at room temperature.

To each panel there was applied a test soil, consisting of pigment dispersed in an oil-solvent system. Specifically, the soil here used was prepared by thoroughly blending the following ingredients:

(a) 1.0 part by weight (pbw) Crisco Oil, a vegetable oil product trademark of and sold by Procter and Gamble Co.;

(b) 1.0 pbw of extra heavy grade Nujol mineral oil, a liquid petrolatum, trademark of and distributed by Plough, Inc., of Memphis, Tenn.;

(c) 1.0 pbw of Tellus ® (Turbine) Oil, a 50/50 blend of 100 HVI (high viscosity index) neutral and 250 HVI neutral oil stocks with an aromatic content of approximately 40 millimoles per 100 grams and a viscosity of about 30 centistokes at 40° C.:

(d) 12.0 pbw jet turbine fuel meeting specification ASTF-640, containing about 18% aromatics, and having a boiling range of about 310°-572° F.;

(e) 20.0 pbw metallic brown pigment, specifically the product of Pfizer, Minerals, Pigments and Metals Division, designated B-01085; and (f) 12.0 pbw of a naphthenic hydrocarbon solvent having a boiling range of about 318°-360° F. and containing about 96% paraffins, 2% aromatics and 2% olefins.

For each test, a linoleum panel is firmly taped to a table top. Between 0.75 and 1.0 cc of the test soil, continually stirred to keep it in a dispersed state, is applied with a dropper down the center of the panel. A 4 inch wide soft rubber printer's roller, previously conditioned by soiling either a previous panel or a scrap piece of linoleum, is run back and forth to spread the soil until it becomes tacky. The soiled panel is cured for one hour at room temperature, then for twenty minutes at 100° C. in a forced-draft oven, and finally conditioned for at least another 2 hours at room temperature.

The cured, soiled panel is placed in the wash tray of a Gardner Straight-Line Washability and Abrasion Machine, model W-G-2000. The panel is then overlaid with an aluminum template (a ⅜ inch thick, 4 inch by 17.5 inch plate having a center cut-out of 2 inches by 16 inches). Clamping of the template to the panel forms a seal around the periphery and a reservoir within the cut-out. A test sponge is mounted within the standard (⅞ inch deep with one open face, nominally 1.5 inch by 3.5 inch) brush holder of the Gardner unit. This sponge is a 1.5 inch by 3.5 inch section cut from a half inch thick sheet of a fine-celled, reticulated, open-pore, chemically-resistant polyurethane foam having 80 pores per lineal inch. The sponge is mounted with a rubber cement or like adhesive on a ⅜ inch by 1.5 inch by 3.5 inch lucite block which fits loosely within the brush holder. Before the test sponge is positioned in the holder, it is saturated with water and shaken hard to release free water.

The template-test panel reservoir is filled with 75 ml of an aqueous solution (or dispersion) of the active detergent component which it is desired to evaluate for hard surface cleaning performance. More particularly, for the present tests this solution contains 0.60% w of a selected ethoxylate component and also 0.12% w of the detergent builder tetrapotassium pyrophosphate. (Control tests were also made in which the 75 ml fill of the reservoir was only water, free of surfactant and builder.)

After the test solution has been allowed to stand in the reservoir for one minute, the test sponge mounted in the Gardner unit is placed on the panel surface and the machine started and run for 100 scrubbing cycles, i.e., 100 passes in each direction. (Adjustment of the scrubbing unit is made to provide a 12.5 inch path of sponge travel within the confines of the template.) After the 100 cycles, the scrubbed panel is removed from the apparatus, rinsed with water, and hung to dry at room temperature for at least one hour.

Reflectance measurements of the scrubbed, dried panel are made in a conventional manner using a Gardner XL-23 Tristimulus Colorimeter. With a light beam of 3.3 cm diameter, four readings are taken in the center portion of the scrubbed path at 5 cm intervals along its length. These readings are averaged to give a single reflectance value for each scrubbed test panel.

Performance of a given ethoxylate composition in the hard surface cleaning test is quantitatively reported in terms of percent soil removed (%SR) according to the equation $$\% SR = \frac{Y_s - Y_{H_2O}}{Y_o - Y_{H_2O}} \times 100$$

wherein $Y_s$ is the average reflectance of the soiled panel after scrubbing with the detergent-containing test composition, $Y_o$ is the average reflectance of the clean panel before application of the test soil, and $Y_{H_2O}$ is the average reflectance after scrubbing of a like soiled panel with only water.

To illustrate distinctions between the critically-defined alkanol ethoxylate compositions of the invention and various ethoxylate-containing compositions not in accordance with the invention, a number of compositions were tested as the surfactant in the above described method. Results of these tests are summarized in the following Table and the attached drawing.

With reference to the drawing, there is depicted a plot containing four curves, each representing hard-surface cleaning performance as a function of HLB value for detergent compositions having one of four different types of ethoxylate components. These four types of ethoxylates, and the performance curves to which they respectively relate are designated A, B, C, and D. With particular reference to the performance curve designated A in the drawing, there is illustrated by this curve the results of the testing of compositions, in accordance with the invention, in which the ethoxylate component was prepared by the general procedures outlined in Examples 1, 2, and 3 above. As shown by curve A, these compositions, when characterized by an HLB value in the range from about 10.4 to 12.0, have beneficial detergent properties not possessed by the other types of compositions tested, containing different ethoxylates as surfactant. Curve B is representative of composition not in accordance with the invention with respect to the proportion of ethoxylate molecules in which the ether substituent is bound to a carbon atom of the alkyl chain which is neither a terminal carbon atom nor a carbon atom adjacent to a terminal carbon atom. Ethoxylate components of the type B compositions are exemplified by the products of the sulfation, hydrolysis and ethoxylation reactions starting with alpha-olefins as illustrated, for instance, by the Comparative Example above. Curve C is representative of detergent compositions formulated from the common commercial primary alkanol ethoxylates which are not in accordance with the invention with respect to the position of ether substitution in the alkyl group of the molecule. In essentially all of the ethoxylate molecules of the type C compositions, the ether substituent is bound to a terminal carbon atom of the alkyl group. Curve D is representative of compositions not in accordance with the invention with respect to their content of compounds having a $C_8$ to $C_{18}$ alkyl group substituted by multiple ether substituents. The ethoxylate components of the type D compositions are commercial secondary alkanol ethoxylates, believed to have been prepared via paraffin oxidation, having a content of the compounds of multiple ether substitution that is about 10 to 15 percent by mol, calculated on mols of alkanol ethoxylate therein. Compositions of type A, B, and C, as tested, were essentially free of such compounds of multiple ether substitution.

The following Table illustrates in more detail distinctions between the compositions of the invention and the other ethoxylate-containing compositions, with respect to several of the characteristics for which criticalities have been observed, and also the influence of these distinctions upon detergent properties of the compositions. In the Table, the tests designated numbers 2, 3, 4 and 10 correspond to the use of detergent compositions prepared from ethoxylate components derived in accordance with the above Examples 1, 3, and 2 and the Comparative Example respectively. In each of the ethoxylate components tested, essentially all of the ethoxylate molecules had an alkyl group (R) of a carbon number in the range from 11 to 15.

wherein R is an alkyl group having a carbon number in the range of from 8 to 18 inclusive, with the further provision that in at least about 50 percent of the ethoxylate molecules R is a linear alkyl group; wherein the $-O$–$(CH_2-CH_2-O)_xH$ ether substituent is bound to R at a carbon atom which is neither a terminal carbon atom nor a carbon atom adjacent to a terminal carbon atom in at least about 40 percent of the ethoxylate molecules; and wherein x has an average value for all molecules of the mixture which is in the range from about 3 to 9 with the further provision that x has a value in the range from 3 to 9 inclusive, in at least about 50 percent of the ethoxylate molecules, (b) said mixture being further characterized as having a hydrophile-lipophile balance that is between about 10.4 and 12.0, said hydrophile-lipophile balance being calculated as 880 times the average value of x for the ethoxylate molecules of the mixture divided by the average molecular weight of the molecules of the mixture, (c) said composition also being characterized as containing less than about 2 percent by mol, calculated on mols of the alkanol ethoxylate mixture therein, of compounds having a $C_8$ to $C_{18}$ alkyl group substituted by multiple ether substituents, and (d) said composition being further characterized as containing the alkanol ethoxylate component in a concentration greater than about 0.06 percent by weight.

2. The composition of claim 1, wherein
R has a carbon number in the range of from 8 to 18, inclusive, in at least about 95 percent of the mole-

TABLE

| | Ethoxylated Component Characterization | | | | | | |
|---|---|---|---|---|---|---|---|
| | | | | Positions of Ether substitutions (% m) | | | |
| Test number | Ethoxylate type | Average HLB value | Average value of X | Terminal carbon atom | Carbon atom adjacent to a terminal carbon atom | Other | Percent soil removed (standardized test) |
| 1 | A | 10.3 | 5.0 | — | — | — | 84 |
| 2* | A | 10.8 | 4.8 | 0 | 37 | 63 | 91 |
| 3* | A | 11.9 | 7.1 | 0 | 20 | 80 | 85 |
| 4* | A | 12.0 | 7.1 | — | — | — | 83 |
| 5 | A | 12.7 | 7.0 | 0 | 37 | 63 | 74 |
| 6 | B | 10.3 | 5.2 | 0 | 74 | 26 | 85 |
| 7 | B | 10.3 | 4.9 | — | — | — | 85 |
| 8 | B | 10.3 | 4.5 | — | — | — | 86 |
| 9 | B | 11.3 | 6.0 | — | — | — | 79 |
| 10 | B | 11.9 | 7.2 | 0 | 74 | 26 | 72 |
| 11 | B | 12.2 | 7.1 | — | — | — | 68 |
| 12 | B | 12.4 | 6.9 | — | — | — | 65 |
| 13 | B | 12.8 | 8.6 | 0 | 74 | 26 | 60 |
| 14 | B | 13.0 | 8.5 | — | — | — | 56 |
| 15 | C | 11.8 | 6.5 | 95+ | — | — | 73 |
| 16 | D | 10.5 | 5.0 | 0 | 20 | 80 | 81 |
| 17** | D | 11.3 | 5.9 | 0 | 20 | 80 | 83 |
| 18 | D | 12.1 | 7.0 | 0 | 21 | 79 | 81 |
| 19 | D | 13.3 | 9.0 | 0 | 21 | 79 | 59 |

*Only the products associated with Tests 2, 3, and 4 are in accordance with the invention.
**A 50/50 blend of the components of test number 16 and test number 18.

We claim as our invention:

1. An alkanol ethoxylate-containing detergent composition, wherein the alkanol ethoxylate component is a mixture of alkanol ethoxylate molecules prepared by an addition reaction between ethylene oxide and the corresponding alkanol, (a) said mixture characterized as consisting essentially of compounds of the formula $$R-O-(CH_2-CH_2-O)_xH,$$

cules of the mixture,
R has a carbon number in the range of from 10 to 18, inclusive, in at least about 70 percent of the molecules of the mixture,
R has a carbon number in the range of from 10 to 16, inclusive, in at least about 50 percent of the molecules of the mixture, and
the ether substituent is bound to R at a carbon atom that is neither a terminal carbon atom nor a carbon atom adjacent to a terminal carbon atom in at least about 50 percent of the ethoxylate molecules.

3. The composition of claim 2, wherein

R has a carbon number in the range of from about 10 to 18, inclusive, in at least about 90 percent of the molecules of the mixture, R has a carbon number in the range of from about 10 to 16, inclusive, in at least about 70 percent of the molecules of the mixture, x has an average value for all molecules of the mixture which is in the range from about 4 to 9, with the further provision that x has a value in the range from 4 to 9, inclusive, in at least about 50 percent of the ethoxylate molecules, and the mixture is characterized as having a hydrophile-lipophile balance that is between about 10.5 and 11.9.

4. The composition of claim 3, wherein

R has a carbon number in the range of from about 10 to 16, inclusive, in at least about 90 percent of the molecules of the mixture, R has a carbon number in the range of from about 11 to 15, inclusive, in at least about 70 percent of the molecules of the mixture, and the mixture is characterized as having a hydrophile-lipophile balance that is between about 10.6 and 11.8.

5. The composition of claim 4, wherein the ether substituent is bound to R at a carbon atom that is neither a terminal carbon atom nor a carbon atom adjacent to a terminal carbon atom in at least about 60 percent of the ethoxylate molecules.

6. The composition of claim 5, wherein R is a linear alkyl group in at least about 70 percent of the ethoxylate molecules.

7. The composition of claim 6, wherein R is a linear alkyl group in at least about 80 percent of the ethoxylate molecules.

8. The composition of claim 1, wherein the composition contains less than about 0.5 percent by weight, calculated on the weight of the alkanol ethoxylate mixture, of polyethylene glycols.

9. The composition of claim 2, wherein the composition contains less than about 0.3 percent by weight, calculated on the weight of the alkanol ethoxylate mixture, of polyethylene glycols.

10. The composition of claim 4, wherein the composition contains less than about 0.3 percent by weight, calculated on the weight of the alkanol ethoxylate mixture, of polyethylene glycols.

11. An alkanol ethoxylate-containing detergent composition, wherein the alkanol ethoxylate component is a mixture of alkanol ethoxylate molecules prepared by an addition reaction between ethylene oxide and the corresponding alkanol, (a) said mixture characterized as consisting essentially of compounds of the formula

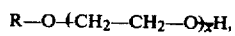

$R-O-(CH_2-CH_2-O)_xH$, wherein R is an alkyl group having a carbon number in the range of from 8 to 18 inclusive, in at least about 98 percent of the molecules of the mixture with the further provisions that in at least about 90 percent of the molecules of the mixture R has a carbon number in the range from 11 to 15, inclusive, and that in at least about 90 percent of the ethoxylate molecules R is a linear alkyl group; wherein the $-O-(CH_2-CH_2-O)_xH$ ether substituent is bound to R at a carbon atom which is neither a terminal carbon atom nor a carbon atom adjacent to a terminal carbon atom in at least about 65 percent of the ethoxylate molecules; and wherein x has an average value for all molecules of the mixture which is in the range from about 4.5 to 9, with the further provision that x has a value in the range from 4 to 9, inclusive, in at least about 50 percent of the ethoxylate molecules, (b) said mixture being further characterized as having a hydrophile-lipophile balance that is between about 10.8 and 11.6 said hydrophile-lipophile balance being calculated as 880 times the average value of x for the ethoxylate molecules of the mixture divided by the average molecular weight of the molecules of the mixture, (c) said composition also being characterized as containing less than about 2 percent by mol, calculated on mols of the alkanol ethoxylate mixture therein, of compounds having a $C_8$ to $C_{18}$ alkyl group substituted by multiple ether substituents, and (d) said composition being further characterized as containing the alkanol ethoxylate component in a concentration greater than about 0.10 percent by weight.

12. The composition of either claim 1, claim 3, claim 5, or claim 7, wherein the composition is characterized as containing less than about 1 percent by mol, calculated on mols of alkanol ethoxylate mixture therein, of compounds having a $C_8$ to $C_{18}$ alkyl group substituted by multiple ether substituents.

13. The composition of either claim 1, claim 3, claim 5, claim 7, or claim 11, wherein the composition is characterized as containing less than about 0.5 percent by mol, calculated on mols of alkanol ethoxylate mixture therein, of compounds having a $C_8$ to $C_{18}$ alkyl group substituted by multiple ether substituents.

14. The composition of either claim 1, claim 3, claim 5, or claim 11, wherein the composition is characterized as containing less than about 0.2 percent by mol, calculated on mols of alkanol ethoxylate mixture therein, of compounds having a $C_8$ to $C_{18}$ alkyl group substituted by multiple ether substituents.

15. The composition of claim 11, wherein the composition contains less than about 0.3 percent by weight, calculated on the weight of the alkanol ethoxylate mixture, of polyethylene glycols.

16. The composition of claim 13, wherein the composition contains less than about 0.3 percent by weight, calculated on the weight of the alkanol ethoxylate mixture, of polyethylene glycols.

* * * * *